US012746364B2

(12) United States Patent
El-Zawahry et al.

(10) Patent No.: US 12,746,364 B2
(45) Date of Patent: Sep. 29, 2026

(54) URINARY CATHETER

(71) Applicant: The University of Toledo, Toledo, OH (US)

(72) Inventors: Ahmed El-Zawahry, Ottawa Hills, OH (US); Benjamin Ogbonna, Toledo, OH (US); Abdullah Nasif, Toledo, OH (US)

(73) Assignee: The University of Toledo, Toledo, OH (US)

( * ) Notice: Subject to any disclaimer, the term of this patent is extended or adjusted under 35 U.S.C. 154(b) by 336 days.

(21) Appl. No.: 18/216,487

(22) Filed: Jun. 29, 2023

(65) Prior Publication Data

US 2024/0066263 A1 Feb. 29, 2024

Related U.S. Application Data

(60) Provisional application No. 63/357,252, filed on Jun. 30, 2022.

(51) Int. Cl.
*A61M 25/00* (2006.01)
*A61M 25/02* (2006.01)

(52) U.S. Cl.
CPC ...... *A61M 25/0017* (2013.01); *A61M 25/008* (2013.01); *A61M 25/02* (2013.01); *A61M 2025/0081* (2013.01); *A61M 2025/0213* (2013.01)

(58) Field of Classification Search
CPC .......... A61M 25/0028; A61M 25/0097; A61M 25/02; A61M 39/22; A61M 39/28; A61M 39/283; A61M 39/284; A61M 39/285; A61M 39/286; A61M 39/287
See application file for complete search history.

(56) References Cited

U.S. PATENT DOCUMENTS

| | | | | | |
|---|---|---|---|---|---|
| 1,719,428 | A | * | 7/1929 | Friedman | A61M 3/0291 604/105 |
| 3,308,825 | A | * | 3/1967 | Cruse | A61M 1/84 606/174 |
| 3,815,608 | A | * | 6/1974 | Spinosa | A61M 25/04 604/105 |
| 4,306,705 | A | * | 12/1981 | Svensson | A61F 5/4405 604/905 |
| 4,465,482 | A | * | 8/1984 | Tittel | A61M 27/00 604/523 |

(Continued)

FOREIGN PATENT DOCUMENTS

| | | | | |
|---|---|---|---|---|
| CN | 104474631 | A | * | 4/2015 |
| CN | 209933783 | U | * | 1/2020 |

(Continued)

*Primary Examiner* — Adam Marcetich
(74) *Attorney, Agent, or Firm* — MacMillan, Sobanski & Todd, LLC

(57) ABSTRACT

The present invention relates to an improved urinary catheter for efficiently draining urine from a urinary bladder of a patient. The improved urinary catheter includes a soft tip that is friendly to the urinary bladder. The improved urinary catheter further includes longer drainage port for proper irrigation of the catheter and thus make it simple to use and better tolerability. In addition, the improved urinary catheter also includes a catheter plug allowing the patient to move more freely and use lavatory rather than using a urine bag all the time.

5 Claims, 11 Drawing Sheets

(56) References Cited

U.S. PATENT DOCUMENTS

| | | | | | |
|---|---|---|---|---|---|
| 4,950,232 | A * | 8/1990 | Ruzicka | A61M 27/006 | 604/43 |
| 4,970,926 | A * | 11/1990 | Ghajar | A61M 25/007 | 83/648 |
| 5,403,291 | A * | 4/1995 | Abrahamson | A61M 25/007 | 604/523 |
| 7,223,263 | B1 * | 5/2007 | Seno | A61M 1/285 | 604/537 |
| 2002/0045855 | A1 * | 4/2002 | Frassica | A61B 1/00148 | 604/103.08 |
| 2003/0135200 | A1 * | 7/2003 | Byrne | A61M 25/007 | 604/329 |
| 2003/0229321 | A1 * | 12/2003 | Simon | A61B 17/3417 | 604/272 |
| 2006/0058702 | A1 * | 3/2006 | Christensen | A61B 5/205 | 600/561 |
| 2006/0157981 | A1 * | 7/2006 | Christensen | A61F 5/4405 | 285/331 |
| 2007/0057222 | A1 * | 3/2007 | Iversen | A61F 5/4405 | 251/324 |
| 2007/0135830 | A1 * | 6/2007 | Schaeffer | A61M 25/0068 | 604/523 |
| 2008/0228174 | A1 * | 9/2008 | Ibrahim | A61M 25/02 | 604/541 |
| 2010/0145265 | A1 * | 6/2010 | Min | A61M 25/1011 | 604/95.03 |
| 2010/0256487 | A1 * | 10/2010 | Hawkins | A61M 25/0028 | 600/434 |
| 2012/0172843 | A1 * | 7/2012 | Sliwa | C23C 28/023 | 604/528 |
| 2013/0172856 | A1 * | 7/2013 | Feri | A61M 25/007 | 604/540 |
| 2015/0202407 | A1 * | 7/2015 | Gonzalez | A61M 25/0017 | 604/544 |
| 2017/0165001 | A1 * | 6/2017 | Lyttle | A61M 25/0158 | |
| 2017/0319373 | A1 * | 11/2017 | Mitts | A61F 5/44 | |
| 2018/0245699 | A1 * | 8/2018 | Lee | F16K 7/06 | |
| 2020/0129676 | A1 * | 4/2020 | Gomez | A61B 17/3423 | |
| 2022/0133979 | A1 * | 5/2022 | Johnsen | B29C 45/0017 | 251/118 |
| 2022/0241551 | A1 * | 8/2022 | Middleton | A61M 25/0147 | |
| 2022/0241552 | A1 * | 8/2022 | Middleton | A61M 25/0021 | |
| 2022/0296355 | A1 * | 9/2022 | Göbel | A61M 25/04 | |
| 2022/0387771 | A1 * | 12/2022 | Cheng | A61M 25/007 | |
| 2023/0001152 | A1 * | 1/2023 | Luque González | A61M 25/0017 | |
| 2024/0123181 | A1 * | 4/2024 | Panesar | A61M 25/008 | |

FOREIGN PATENT DOCUMENTS

| | | | | | |
|---|---|---|---|---|---|
| CN | 112483668 | A | * | 3/2021 | F16K 27/044 |
| CN | 113082472 | A | * | 7/2021 | A61M 25/10 |
| CN | 213608645 | U | * | 7/2021 | |
| CN | 113318325 | A | * | 8/2021 | A61M 25/0043 |
| CN | 113599671 | A | * | 11/2021 | A61M 25/0041 |
| EP | 2872194 | B1 | * | 9/2016 | A61M 25/0017 |
| ES | 2828149 | A1 | * | 5/2021 | A61M 39/22 |
| FR | 2240026 | A1 | * | 3/1975 | A61M 27/00 |
| FR | 2788222 | A1 | * | 7/2000 | A61M 1/3659 |

* cited by examiner

URINARY CATHETER

BACKGROUND AND PRIOR ART

The invention generally relates to the field of catheters. More particularly, the present invention relates to an improved catheter, which is easily manipulatable, safe, simple and reliable in use.

Urethral catheterization is a common medical practice for a variety of problems. Many problems require long-term catheterization such as retention of urine, urinary dysfunction, neurogenic bladder, pelvic floor dysfunction, and enlarged prostate. In addition, urethral catheterization is a conventional preoperative preparation for patients who are subjected to surgery, and is also an important urination means for patients who have difficulty in urination.

Catheters are used in medical practice in hospitals, and nursing homes for draining urine from a urinary bladder. The catheters are required in cases when a person can't empty a urinary bladder, having urinary incontinence and having urinary retention. If the bladder isn't emptied, urine can build up and lead to pressure in the kidneys. The pressure can lead to kidney failure, which can be dangerous and result in permanent damage to the kidneys.

Catheters are a hollow tube used to drain the bladder. There are two principal type of catheter used in the medical industry. One is a single use intermittent catheter, and the other is Foley catheter or urinary catheter. Many people and nursing home residents suffer from urinary issues and live with chronic urinary catheters. They constant use of urine bags all the time leads to limited mobility, depression, falling accident, frustration and neurogenic bladder. The patient can also experience catheter associated complications and urinary tract infections.

A conventional urinary catheter design generally includes a tip and a side opening at a distal end of the catheter. The tip also has a small balloon filled with solution that anchors the catheter in a body of a patient. This prevents the catheter from sliding out of the patient's body. When the catheter needs to be removed, the balloon is deflated. The problem with the tip of the conventional urinary catheter is that the tip is stiff, rigid and firm, thus the stiff tip penetrates the bladder wall causing mucosal tears and edema in the wall of the urinary bladder and thus, causing significant bladder pain and spasm, along with an increased risk of bleeding and infection. The problem with the side opening is that this generates a negative pressure within the urinary bladder.

The conventional urinary catheter has ports at proximal end of the catheter. The proximal end of the catheter has two ports, one is a draining port and other one is a balloon port, for draining and stabilizing the catheter respectively. The location of the ports causes problems. Due to the location of the ports, conventional urinary catheters are difficult to manipulate and also make it difficult to properly irrigate the catheter, changing bags, use catheter plugs and any other maintenance needed for long-term catheter use. The balloon port is very close to the drainage port and has the same length. This makes handling the drainage port difficult for irrigation and for manipulation to change the urinary bags or use a valve, catheter plug etc.

To improve a patient's quality of life, a patient can use an external plug with the conventional urinary catheter. The external plug is connected to the drainage port for collecting urine followed by passing the collected urine into a urine bag. There are problems associated with the external plug; it is difficult to manipulate, difficult to apply, and requires frequent replacement as it is not reusable. The usage of the external plug also leads to leakage and frequent accidents. The alternative of the external plug is that the patient needs to carry the urine bag all the time, which leads to multiple problems and potential side-effects such as quality of life, limited mobility etc. The external plug can be difficult to place as the two ports are very close to each other. Moreover, the patient needs to remove the urine bag before placing the plug in the drainage port. There being a need for an improved catheter and plug that allows patients more freedom to ambulate, thus improving quality of life.

The conventional urinary catheter also requires an external catheter support for supporting the catheter to the body of the patient. The external catheter support may be a support patch, gauze and alike. However, the external catheter support leads to frequent detachment of the catheter from the patient's body.

Therefore, to overcome the shortcomings of the prior art, there is a need to provide a simple to use improved urinary catheter for draining urine from the urinary bladder. Thus, there is a need to provide a single system urinary catheter that does not require any external plug to drain the urine from the catheter and an external support to fix the catheter to the body of the patient.

SUMMARY OF THE INVENTION

The present invention relates to an improved urinary catheter that is simple to use, easy to holster, easy to manipulate and better tolerability for draining urine from the bladder of a patient. The improved urinary catheter includes a catheter shaft having a proximal end and a distal end. The distal end of the catheter shaft includes a tip with multiple narrower holes replacing a single opening enhancing the efficiency of the catheter. The narrower multiple holes in the tip will limit the suction effect of the wide single hole, which is known to cause suction of the mucosa and cause bleeding, spasms and tears. The proximal end of the urinary catheter includes a balloon port on one side and a drainage port on another side of the proximal end of the urinary catheter. In one embodiment of the present invention the drainage port is longer in length than the balloon port. In the preferred embodiment the drainage port is 2-10 centimeters longer than the balloon port. However, it is understood that the length could be adjusted from 1 millimeter to any length. The preferred embodiment is 4-5 centimeters longer than the balloon port.

The improved urinary catheter further includes a catheter plug positioned at the end of the drainage port. The catheter plug will help to facilitate occlusion of the catheter while manipulating the bag, or to remove the bag all together to improve care and mobility. The catheter further includes an anchor for providing support to the urinary catheter and attaching the catheter close to body of the patient. In one embodiment of the present invention, a side anchor is provided for attaching the catheter to the body of the patient. The catheter plug further includes a valve attached to the anchor towards the end of the drainage port allowing the patient to plug or occlude the urinary catheter.

A primary objective of the present invention is to provide a single system urinary catheter that does not require any external plug to drain the urine from the catheter all the time. An objective of the present invention is to provide a user-friendly improved urinary catheter for the patients, care givers and healthcare practitioners thus improving the quality of life of patients and care givers.

Another objective of the present invention is to provide an improved catheter that does not require any external support to hold the catheter in place to the body of the patient.

A further objective of the present invention is to provide an improved urinary catheter for draining urine from the urinary bladder that is simple to use and easy to manipulate.

Another objective of the present invention is to provide an improved urinary catheter that has a softer tip that is friendly to the urinary bladder and minimizes suction of the mucosal layer from the urinary bladder.

A further objective of the present invention is to provide an improved urinary catheter that has longer ports enabling the user better and easier manipulation of the catheter, connect bags and proper irrigation of the catheter.

Another further objective of the present invention is to provide an improved urinary catheter that has valve allowing having the catheter with no bags safely.

In one embodiment of the present invention, the catheter shaft includes a tip with multiple holes allowing easy positioning of the urinary catheter in the urinary bladder.

In one another embodiment of the present invention, the tip includes multiple openings with a spring action.

In another embodiment of the present invention, a catheter plug allows proper draining and irrigation of the urinary catheter. The catheter plug includes a valve to drain and occlude the catheter. The catheter includes an anchor for holding the catheter to the body of the patient and allowing the catheter to be in place. In one another embodiment of the present invention, the anchor is a holster that is used to holster the ports in place to the body of the patient.

In an alternative embodiment the catheter plug could be replaced with an improved lock mechanism to occlude the catheter. A. The catheter lock operates with two cylinders (inner and outer) using a spring-pump mechanism. In the resting state of the catheter lock, the spring is fully extended. The extended state of the spring results in the openings of the two cylinders not being aligned with each other. This purposeful misalignment clamps the catheter, which was passed through the two openings, and prevents urine flow. The inner cylinder has two small arms on the outside that is guided by the slots on the outside of the outer cylinder. This prevents the spring from pushing out the inner cylinder during the unclamped state. When a patient wants to release the urine stored in the bladder and catheter, they can press and hold down on the inner cylinder, which compresses the spring and aligns the openings of the cylinders. The alignment promotes the passage of urine out of the catheter until the patient stops pressing down.

This catheter lock allows the patient to move more freely and perform more daily activities without the nuisance of a urinary bag attached to them. The lock is compact and small which makes it more discreet for patients. Lastly, the push mechanism to allow urine flow out of the catheter gives the patient more control when it comes to emptying their bladder and is less of a hassle compared to the traditional urinary bag.

IN THE DRAWINGS

The objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described and explained with additional specificity and detail through the use of the accompanying drawings in which:

FIG. 1(*b*) illustrates a tip of the conventional urinary catheter;

FIG. 1(*c*) illustrates a pair of ports of the conventional urinary catheter;

FIG. 1(*d*) illustrates an external plug provided on the port of the urinary catheter;

FIG. 1(*e*) illustrates a catheter securing strap provided on the port of the urinary catheter;

FIG. 2(*b*) illustrates detailed view of the improved the urinary catheter focusing on a catheter plug;

FIG. 2(*c*) illustrates an alternative embodiment of the improved urinary catheter;

FIG. 3(*b*) illustrates an anchor of the catheter plug on the drainage port of the urinary catheter;

FIG. 4(*b*) illustrates a soft tip with multiple holes with a spring action; and FIG. 4(*c*) illustrates a top view of the soft tip provided with multiple holes having spring action.

Figure 1A:
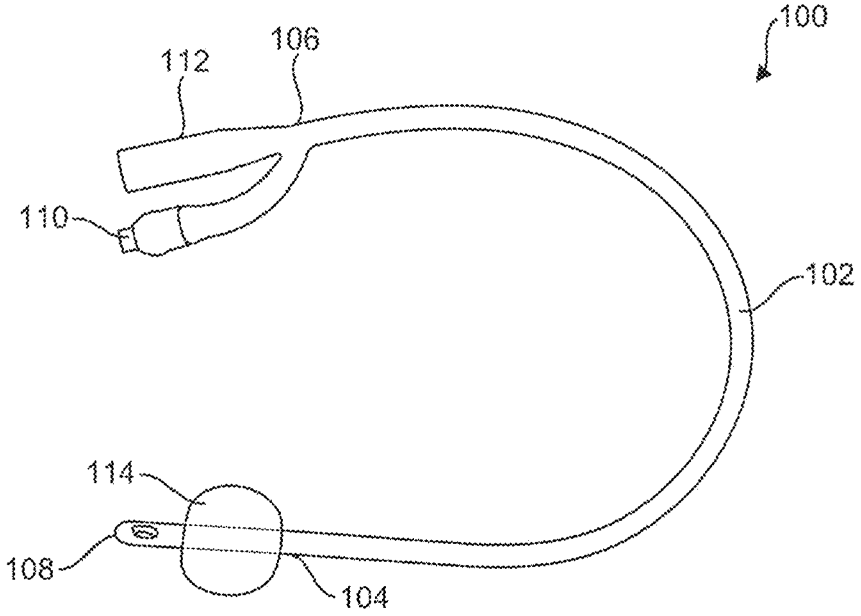
FIG. 1(*a*) illustrates a conventional urinary catheter.
Figure 1B:
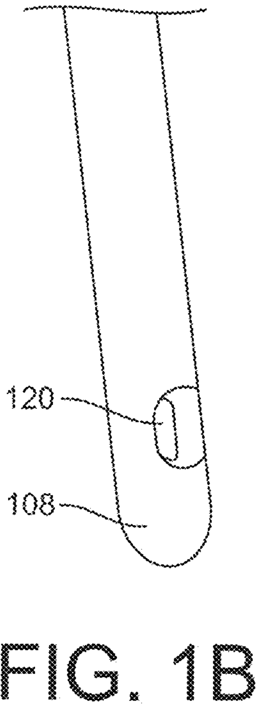
Figure 1C:
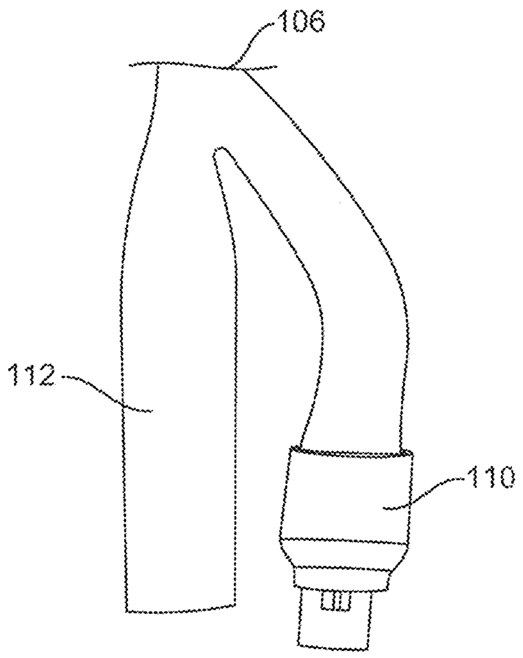
Figure 1D:
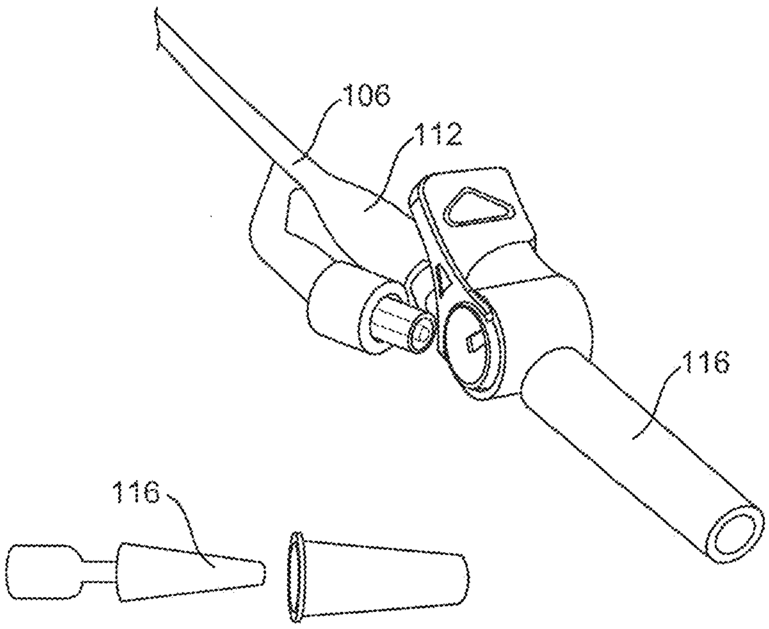
Figure 1E:
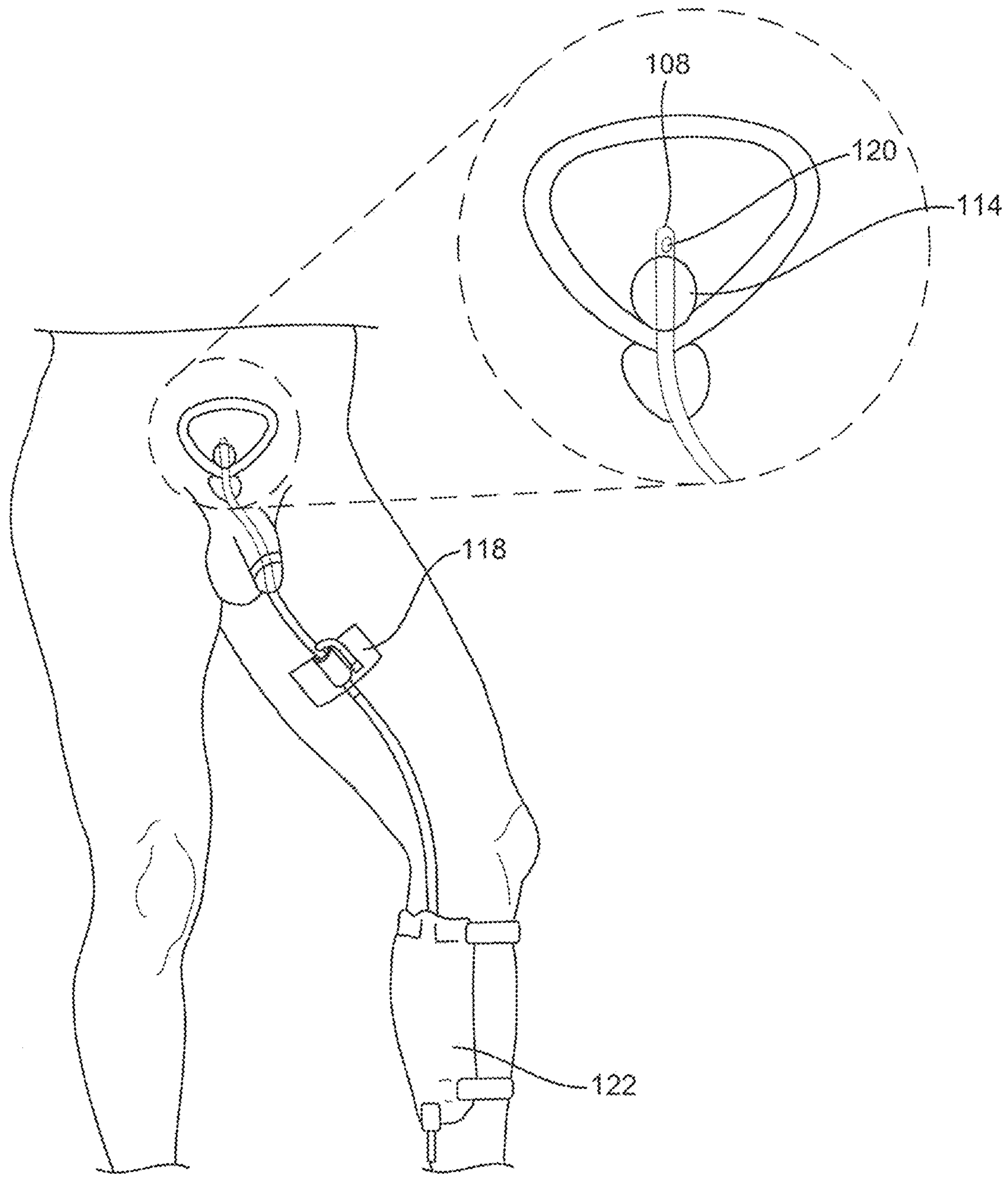

FIG. 5(*a*)-(*f*) illustrates the improved catheter lock mechanism.

DESCRIPTION OF THE INVENTION

A conventional urinary catheter (100) according to conventional design is shown in FIG. 1(*a*)-1(*e*). FIG. 1(*a*) focuses on the conventional urinary catheter (100) includes a catheter shaft (102) having a distal end (104) and a proximal end (106) is disclosed. The distal end (104) further includes a tip (108) that supports the catheter (100) within a urinary bladder of the patient. The proximal end (106) of the conventional urinary catheter (100) includes a balloon port (110) and a drainage port (112) for irrigating and discharging the urine from the catheter (100).

Further, FIG. 1(*b*) focuses on the distal end (104) of the conventional urinary catheter (100). The distal end (104) further includes a tip (108) that supports the catheter (100) within a urinary bladder of the patient. The conventional urinary catheter (100) further includes a retention balloon (114) in proximity of the tip (108), which is filled with solution that anchors the urinary catheter (100) in the urinary bladder of the patient. This prevents the catheter (100) from sliding out of the urinary bladder of the patient. When the catheter needs to be removed, the balloon (110) is deflated.

Further, FIG. 1 (*c*) focuses on the proximal end (106) of the conventional urinary catheter (100). The proximal end (106) of the conventional urinary catheter (100) has two ports; one is the balloon port (110) and the drainage port (112) for irrigating and discharging the urine from the catheter (100) respectively. Further, FIG. 1(*d*) focuses on an external plug (116) that to be attached with the conventional urinary catheter (100). The patient requires the external plug (116) to be connected to the drainage port (112) for storing urine in the bladder during ambulation without or bag. Further, FIG. 1(*e*) focuses on an external catheter support strap (118) for securing the urinary catheter (100) to the patient's thigh or leg.

Figure 2A:
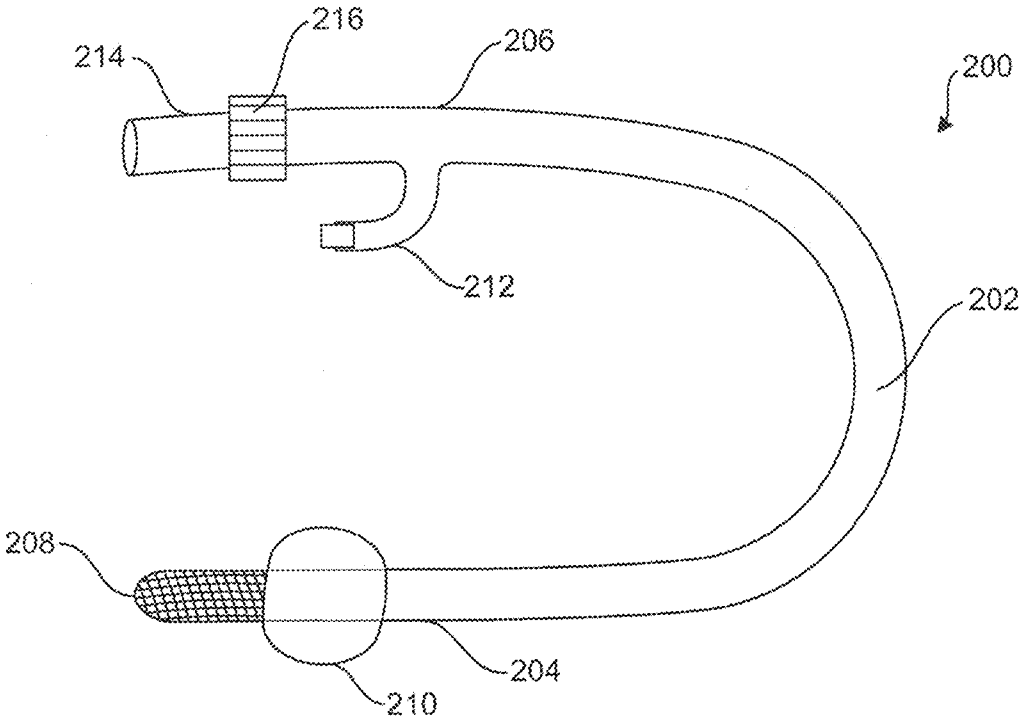
FIG. 2(*a*) illustrates an improved urinary catheter.
Figure 2B:
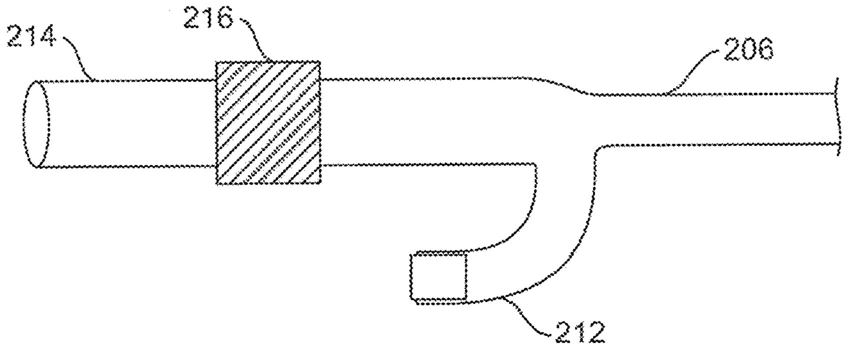
Figure 2C:
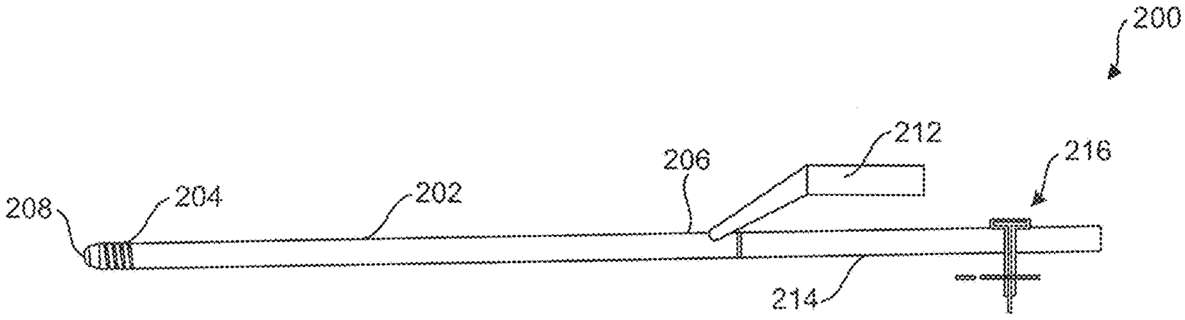

An improved urinary catheter (200) is illustrated in FIG. 2(*a*)-2(*c*). FIG. 2(*a*) primarily focuses on the improved urinary catheter (200) that includes an elongated, flexible, catheter shaft (202) with a distal end (204) and a proximal end (206). The improved urinary catheter (200) further includes a soft tip (208) at the distal end (204) of the catheter (200) for improving the flow and reduces risk to the patient. The soft tip (208) further includes multiple holes replacing a single opening as shown in FIG. 1(*b*). The soft tip (208) also includes a rounded bottom end made of a soft material, thereby removing risk of damage of mucosal layer of the urinary bladder of the patient. The improved urinary catheter (200) is speculated to be made of silicon material or latex free siliconized material and a like material.

The improved urinary catheter (200) further includes a retention balloon (210) in proximity to the soft tip (208) for keeping the catheter (200) seated in the urinary bladder of a patient. The retention balloon (210) when inflated, prevents the improved urinary catheter (200) from sliding out of the body of the patient. When the improved urinary catheter (200) needs to be removed, the retention balloon (210) is deflated.

The improved urinary catheter (200) further includes a balloon port (212) at the proximal end (206) for balloon inflation and deflation, in fluid connection with the retention balloon (210), which can be used for continuous bladder irrigation. The improved urinary catheter (200) further includes a drainage port (214) at the proximal end (206), for draining collected fluid from the urinary bladder of the patient. The drainage port (214) is longer in size than that of balloon port (212) enabling the patient to connect bags easily, thereby allowing proper irrigation and draining of the catheter. Further, the longer size of the drainage port (214) also allows easy manipulation of the catheter by the patient or any healthcare worker, practitioner, doctors and alike.

The improved urinary catheter (200) further includes a catheter plug or valve (216) positioned at the end of the drainage port (214) allowing proper draining and irrigation of the catheter (200). Thus, the improved urinary catheter (200) does not require any external plug for occluding or plugging the drainage port (214). FIG. 2(*b*) focuses on the catheter plug (216) of the urinary catheter that allows proper draining and irrigation of the improved urinary catheter (200), and thus improves mobility of the patient and reduces chances of leakage accidents from the improved urinary catheter (200).

FIG. 2(*c*) illustrates an alternative embodiment of the improved urinary catheter (200) including an elongate, flexible, catheter shaft (202) with a distal end (204) and a proximal end (206). The improved urinary catheter (200) further includes a soft tip (208) at the distal end (204) of the catheter (200) for improving the flow and reduces risk of bladder injuries and trauma to the patient. The soft tip (208) further includes multiple holes or fenestrations replacing a single opening as illustrated in FIG. 1(*b*). The multiple holes also include a spring-like action for improving quality of the catheter tip and minimize trauma from the catheter tip. The catheter is retained within the urinary bladder of the patient by the retention balloon (112) as illustrated in FIG. 1(*a*). The soft tip (208) also includes a rounded bottom end made of a soft material, thereby removing risk of damage of mucosal layer of the urinary bladder of the patient replacing stiff or rigid bottom end as illustrated in FIG. 1(*b*).

The improved urinary catheter (200) further includes a balloon port (212) at the proximal end (206) for balloon inflation, in fluid connection with the retention balloon (210), which can be used for catheter retaining in the bladder. The improved urinary catheter (200) further includes a drainage port (214) at the proximal end (206), for draining collected fluid from the urinary bladder of the patient. The drainage port (214) is longer in size than that of balloon port (212) enabling the patient to perform simple manipulation, connect or disconnect bags easily, thereby allowing proper manipulation, irrigation and draining of the catheter. Further, the longer size of the drainage port (214) also allows easy manipulation of the catheter by the patient or any healthcare worker, practitioner, doctors and alike. The drainage port (216) is longer by 1 cm-10 cm, preferably 3.5 cm-5 cm in length to the balloon port (212).

The improved urinary catheter (200) further includes a catheter plug (216) positioned at the end of the drainage port (214) allowing proper draining and irrigation of the catheter (200). Thus, the improved urinary catheter (200) does not require any external plug for occluding or plugging the drainage port (214). The catheter plug (216) further includes a valve to plug or occlude the improved catheter (200). The catheter plug (216) includes an anchor for holding the improved catheter (200) to the body of the patient and allowing the improved catheter (200) to be in place. In one another embodiment of the present invention, the anchor is a holster that is used to secure the ports in place to the body of the patient.

Figure 3A:
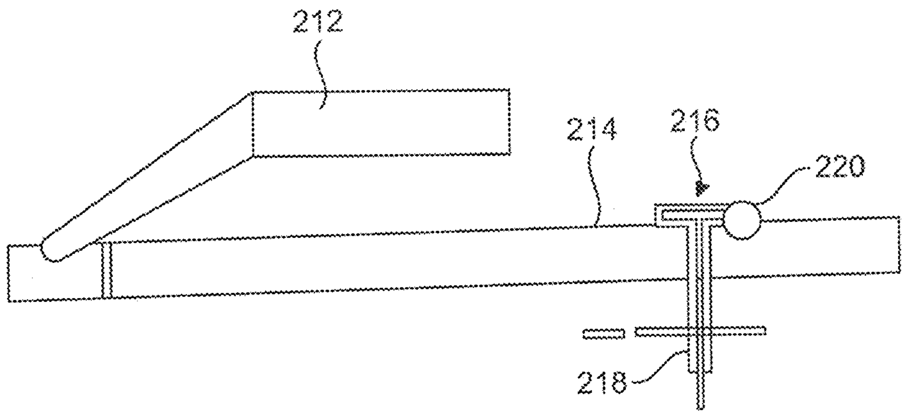
FIG. 3(*a*) illustrates a valve of the catheter plug provided on the drainage port of the urinary catheter.
Figure 3B:
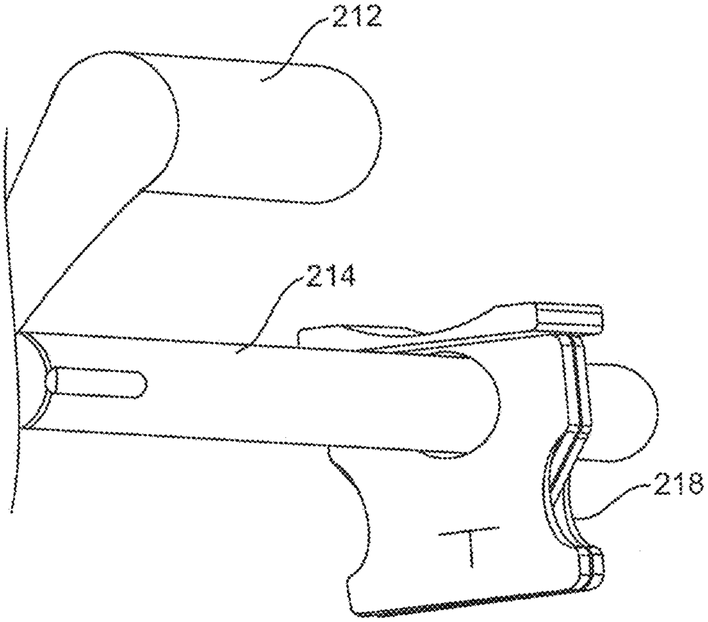

FIG. 3(*a*) illustrates a detailed view of the catheter plug (216) that is disposed on the drainage port (214) allowing proper draining and irrigation of the improved urinary catheter (200). The catheter plug (216) replaces the need of the external plug (116) as illustrated in the FIG. 1(*d*) for draining of the catheter (200) as the drainage port (214) is longer as compared to the drainage port (114) of conventional urinary catheter (100) as illustrated in FIG. 1(*b*).

The catheter plug (216) includes an anchor (220) for holding the improved catheter (200) to the body of the patient and allowing the improved catheter (200) to be in place by replacing the catheter securing strap (118) as illustrated in FIG. 1(*e*). The anchor (220) is a holster that is used to secure the catheter (200) in place to the body of the patient and thus allowing the patient to use lavatory instead of the urine bag.

Further, the catheter plug (216) includes a valve (218) attached to the anchor (220) towards the end of the drainage port (214) allowing the patient to plug or occlude the improved urinary catheter (200). Further, FIG. 3(*a*) also focuses on the valve (218) attached to the anchor (220) allowing the patient or any person to plug or occlude the improved urinary catheter (200).

Further, FIG. 3(*b*) focuses on the anchor (220) that is used for holding the improved catheter (200). The anchor (220) positioned on the longer drainage port (214) and configured for holding the improved catheter (200) to the body of the patient and thus allowing the improved catheter (200) to be in place by replacing the catheter securing strap (118) as illustrated in FIG. 1(*e*). The anchor (220) is a holster that is used to secure the catheter (200) in place to the body of the patient and thus allowing the patient to use lavatory instead of the urine bag.

Figure 4A:
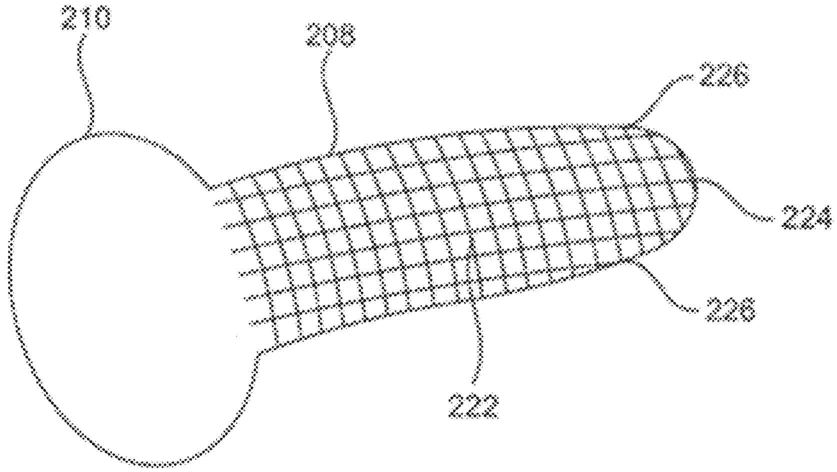
FIG. 4(*a*) illustrates a soft tip with multiple holes.
Figure 4B:
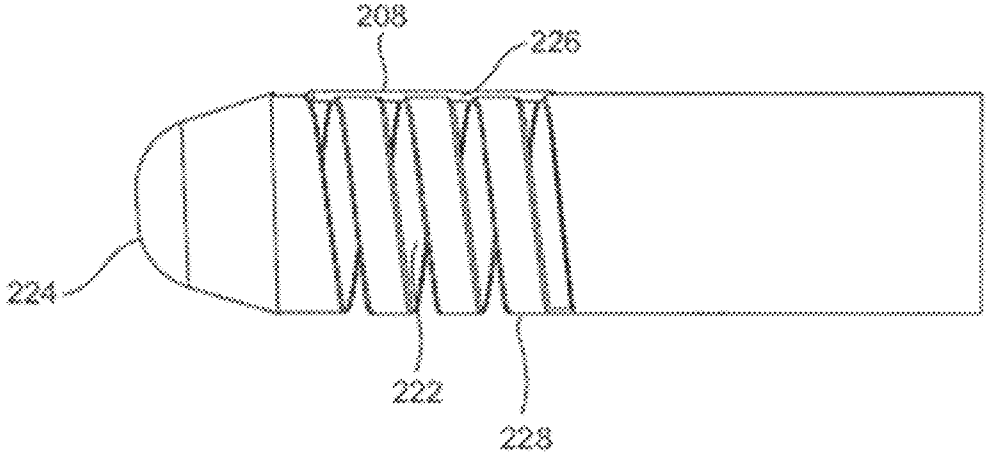
Figure 4C:
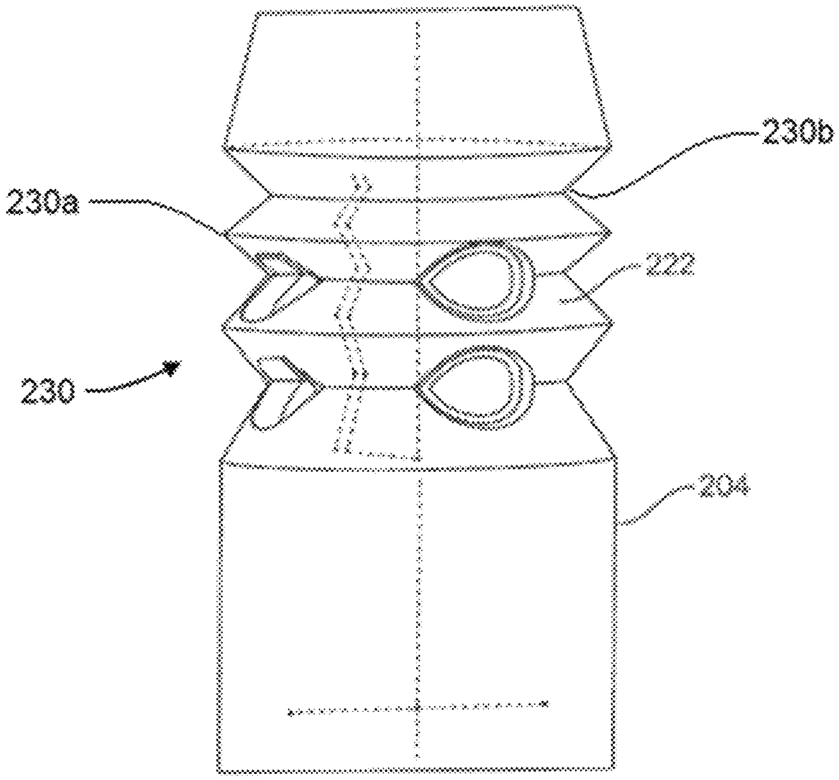
Figure 5A:
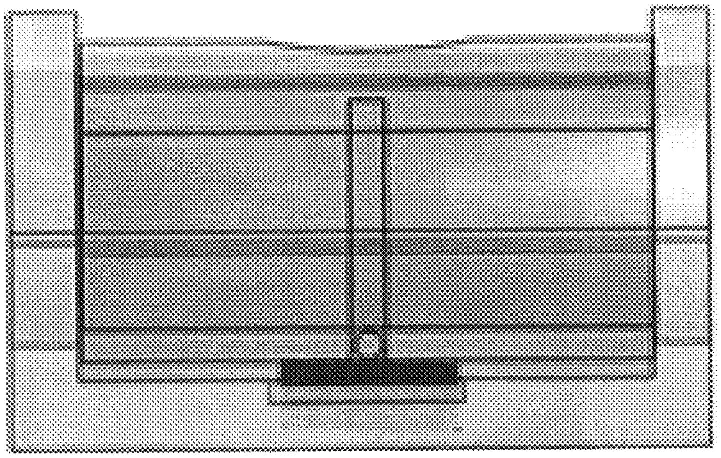
Figure 5B:
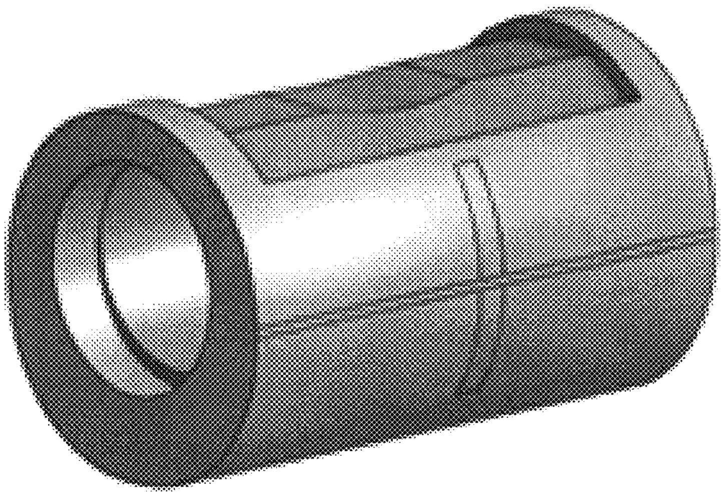
Figure 5C:
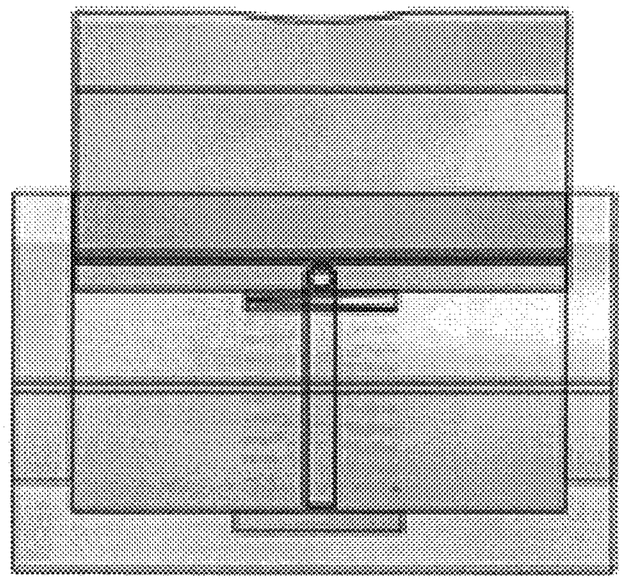
Figure 5D:
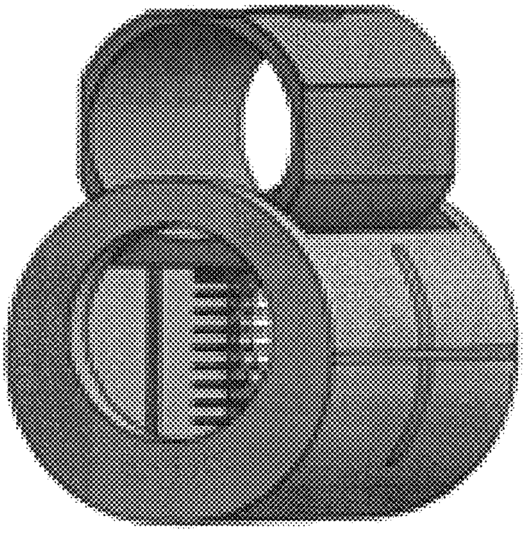
Figure 5E:
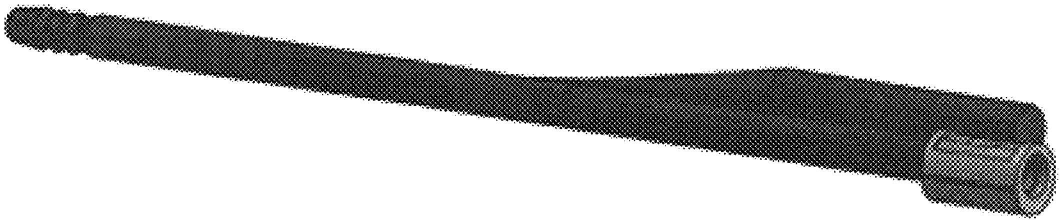
Figure 5F:
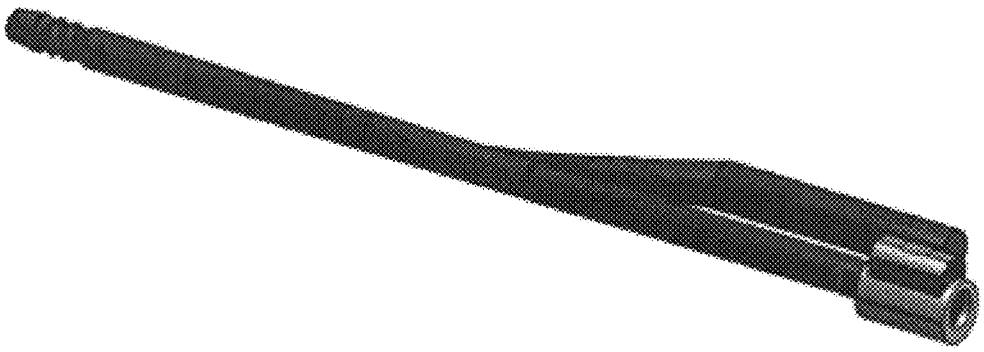

FIG. 4(*a*) illustrates a detailed view of the soft tip (208) provided at the distal end (204) of the improved urinary catheter (200) according to one embodiment of the present invention. The soft tip (208) improves retention of the improved urinary catheter (200) within the urinary bladder of the patient. The soft tip (208) is modified in such a way that it is friendly to the urinary bladder of the patient and prevents damage of mucosal layer of the urinary bladder of the patient and thus minimizing suction of the mucosal layer of the urinary bladder.

The soft tip (208) includes multiple holes or fenestrations (222) replacing a single opening as illustrated in FIG. 1(*b*).

The soft tip (208) includes a rounded bottom end (224) that is soft enough, contrary to the previous general belief in the field, has a very limited risk of damaging mucosal layer during insertion. The soft tip (208) automatically finds a way through the difficult passages of the urethra, and smoothly enters, and without any risk of penetrating the urethra. The risk for penetration of the urethral wall is also lowered, which is of particularly useful for users having no or reduced sensitivity in the urethra tract. The soft tip (208) further includes a pair of side walls (226) that are thick as compared to the rounded bottom end (224), thereby providing a grip and support to the catheter (200) within the urinary bladder of the patient.

FIG. 4(*b*) illustrates a detailed view of the soft tip (208) provided at the distal end (204) of the improved urinary catheter (200) according to alternative embodiment of the present invention. The soft tip (208) includes multiple holes or fenestrations (222) minimizing suction of the mucosal layer of the bladder of the patient. The soft tip (208) includes a rounded bottom end (224) that is soft enough, that it automatically finds a way through the difficult passages of the urethra, and smoothly enters, and without any risk of penetrating the urethra. The tip (208) is configured as a helical thread form (228) that defines interstitial helical spaces between adjacent helical thread segments (228) forming the fenestrations (222). The helical thread form (228) is supported by at least one side wall (226) extending across the helical thread form (228) to support and maintain the position of the fenestrations (222). The at least one side wall (226) is configured as a bar or elongate crossmember that maintains a flexure characteristic of the helical thread form (228).

FIG. 4(*c*) focuses on top view of the soft tip (208) having a spring action allowing the improved urinary catheter (200) to be in place. The multiple holes also include a spring for improving the retention of the catheter within the urinary bladder of the patient by replacing the retention balloon (112) as illustrated in FIG. 1 (*a*). The soft tip (208) also includes a rounded bottom end (224) made of a soft material, thereby removing risk of damage of mucosal layer of the urinary bladder of the patient replacing stiff or rigid bottom end as illustrated in FIG. 1 (*b*). As shown in FIG. 4 (*c*), the soft tip (208) is configured as an accordion or bellows spring defining convolutions or pleats (230). Each pleat (230) includes a major diameter or crest (230*a*) and a minor diameter or root (230*b*) forming a pleated depression of the bellows structure. The illustrated fenestrations or small holes (222) are formed in the root (230*b*) to fluidically connect the tip to the hollow interior of the catheter shaft (202).

The invention claimed is:

1. A urinary catheter comprising;

a catheter shaft with a proximal end and a distal end;

the distal end comprising;

a tip having an helical thread form defining a singular helical space extending along the helical thread form and configured to remove urine from a patient's bladder;

at least one side wall extending over the helical thread form and configured to support the helical thread form during insertion;

a balloon located adjacent to the helical thread form and capable of being filled and drained of solution, the proximal end comprising:

a balloon port on one side of the proximal end;

an anchor for providing support to the urinary catheter;

a drainage port on another side of the proximal end, wherein the drainage port is longer than the balloon port by 2-10 cm; and a catheter plug positioned at the end of the drainage port, wherein the catheter plug includes a valve attached to the drainage port, wherein the valve allows the patient to plug or occlude the urinary catheter.

2. The urinary catheter of claim 1 wherein the tip is flexible and pliable.

3. The urinary catheter of claim 1 wherein the drainage port is longer than the balloon port by 4-5 cm.

4. The urinary catheter of claim 1 wherein the side wall is configured to extend through sections of the helical thread form and adjacent sections of the singular helical space.

5. The urinary catheter of claim 1 wherein the side wall is configured as segments extending between adjacent sections of the helical thread form.

* * * * *